United States Patent
Liu et al.

(10) Patent No.: US 7,383,731 B2
(45) Date of Patent: Jun. 10, 2008

(54) DEEP-FRY OIL QUALITY SENSOR

(75) Inventors: James Z T Liu, Belvidere, IL (US);
Steven J. Magee, Lena, IL (US);
James D. Cook, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 175 days.

(21) Appl. No.: 11/145,461

(22) Filed: Jun. 2, 2005

(65) Prior Publication Data

US 2006/0272415 A1 Dec. 7, 2006

(51) Int. Cl.
*G01N 29/06* (2006.01)
*G01N 29/40* (2006.01)

(52) U.S. Cl. ............... 73/602; 73/54.25; 73/54.01; 73/54.41; 73/64.53

(58) Field of Classification Search ............ None
See application file for complete search history.

(56) References Cited

U.S. PATENT DOCUMENTS

| | | | | |
|---|---|---|---|---|
| 4,691,714 | A | 9/1987 | Wong et al. | 128/738 |
| 5,117,146 | A * | 5/1992 | Martin et al. | 310/313 R |
| 5,130,257 | A * | 7/1992 | Baer et al. | 436/151 |
| 5,235,235 | A | 8/1993 | Martin et al. | 310/313 D |
| 5,629,039 | A | 5/1997 | Brintle | 426/417 |
| 5,701,807 | A | 12/1997 | Park | 99/422 |
| 5,869,763 | A | 2/1999 | Vig et al. | 73/580 |
| 6,044,332 | A | 3/2000 | Korsah et al. | 702/76 |
| 6,076,406 | A | 6/2000 | Blair et al. | 73/590 |

(Continued)

FOREIGN PATENT DOCUMENTS

| | | |
|---|---|---|
| GB | 2236591 A | 4/1991 |
| JP | 2003250708 A | 9/2003 |
| WO | WO 98/37412 * | 8/1998 |

OTHER PUBLICATIONS

Benedito et al., "Ultrasonic Assessment of Oil Quality during Frying", Jun. 2002, Journal of Agricultural and Food Chemistry, vol. 50, No. 16, pp. 4531-4536.*
McClements D J et al., Ultrasonic Analysis of Edible Fats and Oils, Ultrasonics, IPC Science and Technology Press, Guildford, GB, vol. 30, No. 6, Jan. 1992, pp. 383-388.
Reindl L et al., SAW Devices as Wireless Passive Sensors, Ultrasonics Symposium, IEEE, NY, USA, vol. 1, Nov. 1996, pp. 363-367.
Bill Drafts, Acoustic Wave Tecnology Sensors, IEEE Transactions on Microwave Therory and Techniques, NJ, USA, vol. 49, No. 4, Apr. 2001, p. 801.

*Primary Examiner*—Hezron E. Williams
*Assistant Examiner*—Rose M Miller
(74) *Attorney, Agent, or Firm*—Kermit D. Lopez; Luis M. Ortiz (57) ABSTRACT

A cooking oil quality sensing apparatus and system includes an acoustic wave sensor composed of one or more acoustic wave transducers configured upon a piezoelectric substrate such that when the acoustic wave sensor is in contact with cooking oil, the sensor generates acoustic wave data indicative of the quality of the cooking oil. An antenna can be integrated with the acoustic wave sensor, such that the antenna receives data an external source and transmits the acoustic wave data indicative of the quality of the cooking oil to the external source. An oscillator can be integrated with the acoustic wave sensor, such that the output of the oscillator contains data indicative of the quality of the cooking oil. The acoustic wave sensor can be coated with a material that is selectively sensitive and/or reactive to one or more fatty acids associated with or contained in the cooking oil.

15 Claims, 9 Drawing Sheets

U.S. PATENT DOCUMENTS

| | | | |
|---|---|---|---|
| 6,293,136 B1 | 9/2001 | Kim | 73/19.03 |
| 6,368,648 B1 | 4/2002 | Bertram et al. | 426/417 |
| 6,469,521 B1 | 10/2002 | Klun et al. | |
| 6,482,326 B2 | 11/2002 | Munson et al. | 210/663 |
| 6,543,274 B1 * | 4/2003 | Herrmann et al. | 73/32 A |
| 6,792,983 B2 | 9/2004 | Allora | 141/98 |
| 6,800,316 B1 | 10/2004 | Perrut et al. | 426/417 |
| 2006/0096357 A1 * | 5/2006 | Andle | 73/54.41 |

* cited by examiner

DEEP-FRY OIL QUALITY SENSOR

TECHNICAL FIELD

Embodiments are generally related to sensing devices and components thereof. Embodiments also relate to oil quality detection device and in particular sensor for detecting the quality of cooking oil. Embodiments additionally relate to acoustic waves sensing components and devices thereof. Embodiments additionally relate to the wireless transmission of detection data.

BACKGROUND OF THE INVENTION

Acoustic wave sensors are utilized in a variety of sensing applications, such as, for example, temperature and/or pressure sensing devices and systems. Acoustic wave devices have been in commercial use for over sixty years. Although the telecommunications industry is the largest user of acoustic wave devices, such devices are also utilized for sensor applications (e.g., chemical vapor detection). Acoustic wave sensors are so named because they use a mechanical, or acoustic, wave as the sensing mechanism. As the acoustic wave propagates through or on the surface of the material, any changes to the characteristics of the propagation path affect the velocity and/or amplitude of the wave.

Changes in acoustic wave characteristics can be monitored by measuring the frequency or phase characteristics of the sensor and can then be correlated to the corresponding physical quantity or chemical quantity that is being measured. Virtually all acoustic wave devices and sensors utilize a piezoelectric crystal to generate the acoustic wave. Three mechanisms can contribute to acoustic wave sensor response, i.e., mass-loading, visco-elastic and acousto-electric effect. The mass-loading of chemicals alters the frequency, amplitude, and phase and Q value of such sensors. Most acoustic wave chemical detection sensors, for example, rely on the mass sensitivity of the sensor in conjunction with a chemically selective coating that absorbs the vapors of interest resulting in an increased mass loading of the acoustic wave sensor.

Examples of acoustic wave sensors include acoustic wave detection devices, which are utilized to detect the presence of substances, such as chemicals, or environmental conditions such as temperature and pressure. An acoustical or acoustic wave (e.g., SAW/BAW) device acting as a sensor can provide a highly sensitive detection mechanism due to the high sensitivity to surface loading and the low noise, which results from their intrinsic high Q factor. Surface acoustic wave devices are typically fabricated using photolithographic techniques with comb-like interdigital transducers placed on a piezoelectric material. Surface acoustic wave devices may have either a delay line or a resonator configuration. Bulk acoustic wave device are typically fabricated using a vacuum plater, such as those made by CHA, Transat or Saunder. The choice of the electrode materials and the thickness of the electrode are controlled by filament temperature and total heating time. The size and shape of electrodes are defined by proper use of masks.

Based on the foregoing, it can be appreciated that acoustic wave devices, such as a surface acoustic wave resonator (SAW-R), surface acoustic wave delay line (SAW-DL), surface transverse wave (STW), bulk acoustic wave (BAW), can be utilized in various sensing measurement applications. One of the primary differences between an acoustic wave sensor and a conventional sensor is that an acoustic wave sensor can store energy mechanically. Once such a sensor is supplied with a certain amount of energy (e.g., through RF), the sensor can operate for a time without any active part (e.g., without a power supply or oscillator). This feature makes it possible to implement an acoustic wave sensor in an RF powered passive and wireless sensing application.

One promising application for micro-sensors involves oil quality monitoring, particularly in the area of deep fry oil cooking implements. Restaurants and food industries currently rely on cooking oil color and foaminess as indicators of oil quality. Researchers have indicated however, that these factors are not sufficient to determine the quality of cooking oil. It has been estimated that twenty-five percent of cooking oil can be converted to free fatty acids and other unhealthy compounds before the color of the cooking oil actually changes. This means that fried foods may be cooked unknowingly in oil of an unacceptable quality, which can ultimately lead to immediate and long term trouble for the consumer. For example, if the oil is rancid, the consumer may become sick. Alternatively, long term health problems associated with consuming unhealthy compounds from poor quality oil may also result.

Chemical changes that take place in cooking oil can make food cooked in such oil harmful to the consuming public. During the heating process, for example, hundreds of reactions take place in the cooking oil. Some of the products of these reactions escape in the form of gases, while others remain in the cooking oil. Remaining compounds include decomposition products and free fatty acids—the building blocks of oil, which are ultimately toxic to the human body. Such fatty acids, for example, cause the upset-stomach feeling that a typical consumer experiences following digestion of fried food.

What is needed to address such problems is the implementation of an oil quality sensor, particularly one which can be monitored wirelessly. It is believed that the embodiments disclosed herein address these long felt needs.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved sensing device.

It is another aspect of the present invention to provide for an acoustic wave sensing device adapted for oil quality detection.

It is yet another aspect of the present invention to provide for a deep-fry oil quality sensor utilizing acoustic wave sensing components.

The aforementioned aspects and other objectives and advantages can now be achieved as described herein. A cooking oil quality sensing apparatus and system are disclosed. In general, an acoustic wave sensor comprising one or more acoustic wave transducers configured upon a piezoelectric substrate can be provided, such that when the acoustic wave sensor is in contact with cooking oil, the sensor generates acoustic wave data indicative of the quality of the cooking oil. An antenna can be integrated with the acoustic wave sensor, such that the antenna receives data from an external source and transmits the acoustic wave data indicative of the quality of the cooking oil to the external source. The acoustic wave sensor can be coated with a material that is selectively sensitive and/or reactive to one or more fatty acids associated with or contained in the cooking oil.

Additionally, depending upon the particular implementation along with design considerations, a frying pan for maintaining and heating the cooking oil, can be provided, wherein the acoustic wave sensor is incorporated into the frying pan in order to detect the acoustic wave data indicative of the quality of the cooking oil. Additionally, a transmitter and receiver unit for transmitting data wirelessly to and from the acoustic wave sensor can be provided along with a pattern recognition module that based on one or more signals transmitted by the antenna from the acoustic wave sensor recognizes varying degrees of quality of the cooking oil.

The acoustic wave transducer(s) configured upon the piezoelectric substrate can be, for example, a bulk acoustic wave (BAW) sensing element, a shear horizontal surface acoustic wave (SH-SAW) sensing element, an acoustic plate mode (APM) sensing element, a shear horizontal acoustic plate mode (SH-APM) sensing element, a surface transverse wave (STW) sensing element, or a flexural plate wave (FPW) sensing element, and/or simply a standard surface acoustic wave (SAW) sensing element.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
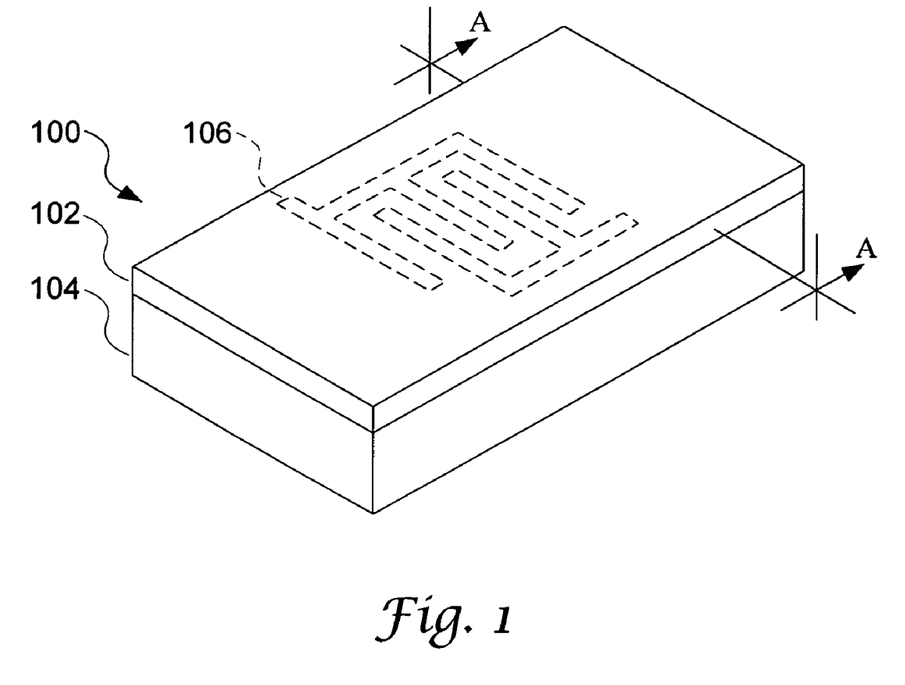
FIG. 1 illustrates a perspective view of an acoustic wave device, which can be implemented in accordance with one embodiment.

FIG. 1 illustrates a perspective view of an acoustic wave device 100, which can be implemented in accordance with one embodiment. Acoustic wave device 100 generally includes an interdigital transducer 106 formed on a piezoelectric substrate 104. The surface wave device 100 can be implemented in the context of a sensor chip. Interdigital transducer 106 can be configured in the form of an electrode, depending upon design considerations. Although only a single electrode or interdigital transducer 106 is depicted in FIG. 1, it can be appreciated that multiple transducers can be implemented upon substrate 104, depending upon the goals and designs of the sensing application. The interdigital transducer 106 can be coated with a coating 102 formed from a material that is selectively sensitive and/or reactive to fatty acids and can be used as an etch rate monitor or fatty acids monitor, depending upon design considerations.

Note that the interdigital acoustic wave device 100 represents only one type of acoustic wave device that can be adapted for use with the embodiments disclosed herein. For example, acoustic wave device 100 may be based on surface acoustic wave (SAW) detection. In such a scenario, transducer 106 may be configured as SAW transducer. It can be appreciated that a variety of other (e.g., SH-SAW, BAW, APM, SH-APM, FPW, SH-SAW-DL, SH-SAW-R, etc.) transducer types can be utilized in accordance with the embodiments described herein. The acoustic wave element or transducer 106 can, for example, be implemented as such as a surface acoustic wave resonator (SAW-R), surface acoustic wave delay line (SAW-DL), surface transverse wave (STW), bulk acoustic wave (BAW), and/or other type of transducer component. Additionally, acoustic wave device 100 can be implemented in a variety of shapes and sizes. The same properties can apply to the configuration depicted in FIGS. 3-4.

Figure 2:
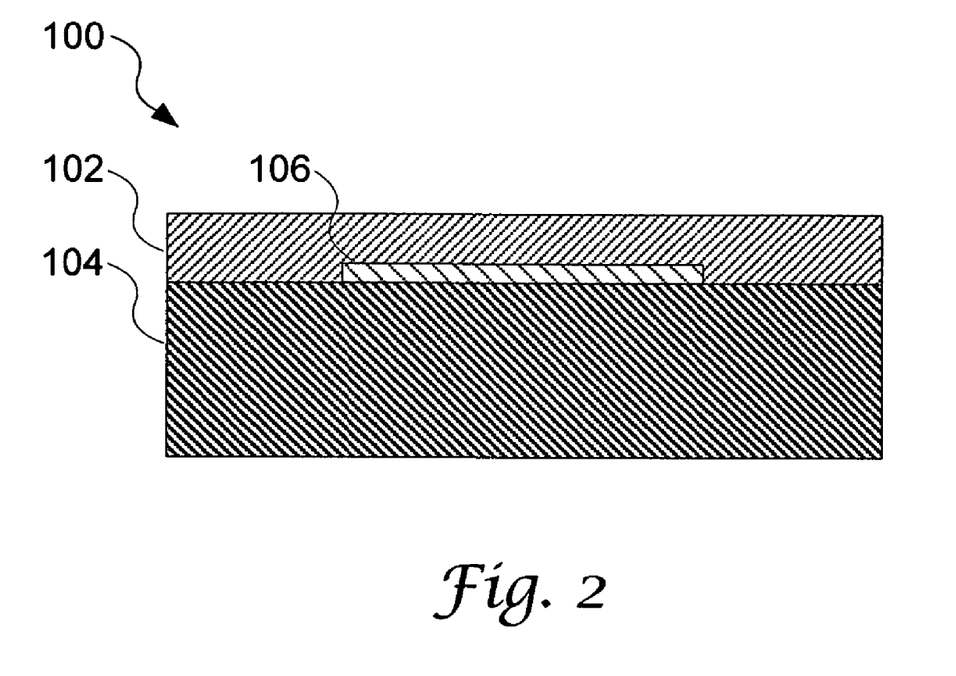
FIG. 2 illustrates a cross-sectional view along line A-A of the acoustic wave device depicted in FIG. 1, in accordance with one embodiment.

FIG. 2 illustrates a cross-sectional view along line A-A of the interdigital acoustic wave device 100 depicted in FIG. 1, in accordance with one embodiment of the present invention. Piezoelectric substrate 104 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few. Interdigital transducer 106 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAl. Third, interdigital transducer 106 can be formed from metal-nonmetal compounds (e.g., ceramic electrodes based on TiN, $CoSi_2$, or WC).

A coating 102 need not cover the entire planar surface of the piezoelectric substrate 104, but can cover only a portion thereof, depending upon design constraints. Coating 102 can function as a protecting layer or a guiding layer, which is shown in greater detail herein with respect to FIG. 5. Selective coating 102 can cover interdigital transducer 106 and the entire planar surface of piezoelectric substrate 104. The acoustic wave device 100 may function as a multiple mode sensing device, excited multiple modes thereof generally occupy the same volume of piezoelectric material. Multiple modes excitation allows separations of temperature change effects from pressure change effects. The multi-mode response can be represented by multiple mode equations, which can be solved to separate the response due to the temperature and pressure.

Figure 3:
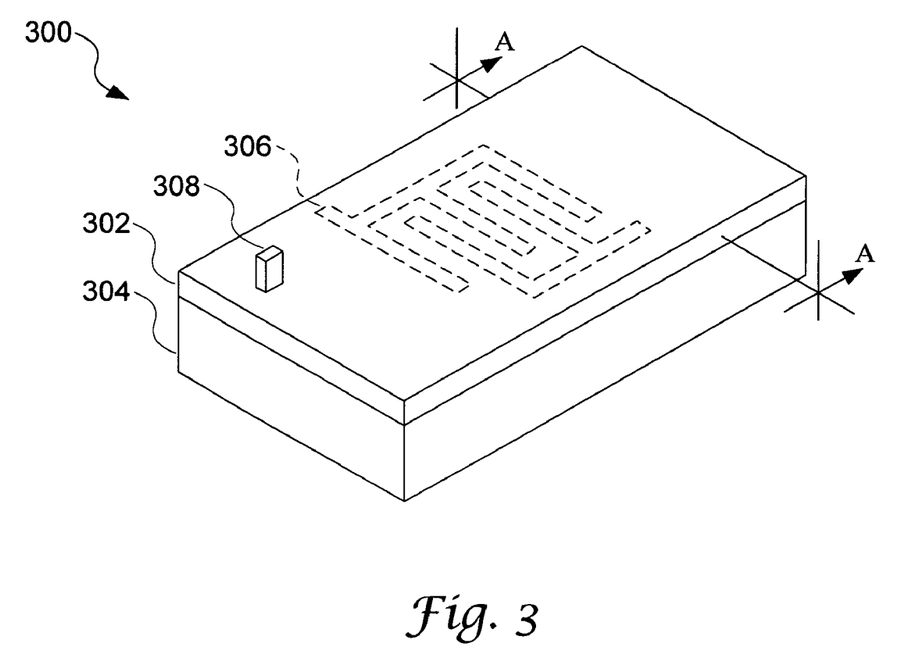
FIG. 3 illustrates a perspective view of an acoustic wave device, which can be implemented in accordance with an embodiment.
Figure 4:
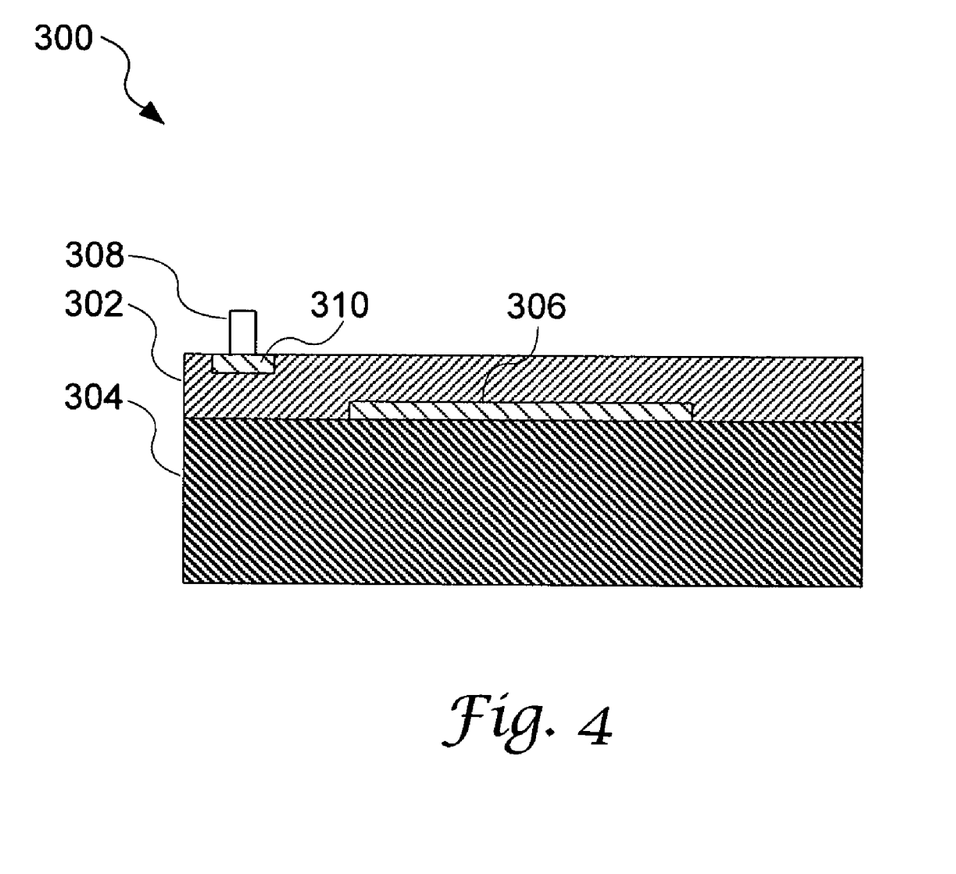
FIG. 4 illustrates a cross-sectional view along line A-A of the acoustic wave device depicted in FIG. 3, in accordance with one embodiment.

FIG. 3 illustrates a perspective view of an acoustic wave device 300, which can be implemented in accordance with an embodiment. The configuration depicted in FIGS. 3-4 is similar to that illustrated in FIGS. 1-2, with the addition of an antenna 308, which is connected to and disposed above a wireless excitation component 310 (i.e., shown in FIG. 4). The antenna 308 can be, for example, a linear type antenna, or a coupler type antenna depending upon design considerations. Surface wave device 300 generally includes an interdigital transducer 306 formed on a piezoelectric substrate 304.

Acoustic wave device 300 can therefore function as a sensing device, based on for example, SAW, BAW and other such transducer components. Interdigital transducer 306, for example, can be configured in the form of an electrode (e.g., BAW, SAW, etc.). A coating 302 can be selected such that a particular species to be measured is absorbed by the coating 302, thereby altering the acoustic properties of the acoustic wave device 300. Various selective coatings can be utilized to implement coating 302. Note that coating 302, which is analogous to coating 102 described earlier can comprise a material that is selectively sensitive and/or reactive to fatty acids and can be used as an etch rate monitor or fatty acids monitor, depending upon design considerations. A change in acoustic properties can be detected and utilized to identify or detect the substance or species absorbed and/or adsorbed by the coating 302. Acoustic wave device 300 can be excited via wireless means (e.g., antenna 308) to implement a surface acoustical model.

FIG. 4 illustrates a cross-sectional view along line A-A of the acoustic wave device 300 depicted in FIG. 3, in accordance with one embodiment of the present invention. Thus, antenna 308 is shown in FIG. 4 disposed above coating 302. Similar to the configuration of FIG. 2, Piezoelectric substrate 304 can be formed from a variety of substrate materials, such as, for example, quartz, lithium niobate ($LiNbO_3$), lithium tantalite ($LiTaO_3$), $Li_2B_4O_7$, $GaPO_4$, langasite ($La_3Ga_5SiO_{14}$), ZnO, and/or epitaxially grown nitrides such as Al, Ga or Ln, to name a few. Interdigital transducer 306 can be formed from materials, which are generally divided into three groups. First, interdigital transducer 106 can be formed from a metal group material (e.g., Al, Pt, Au, Rh, Ir Cu, Ti, W, Cr, or Ni). Second, interdigital transducer 106 can be formed from alloys such as NiCr or CuAl. Third, interdigital transducer 306 can be formed from metal-nonmetal compounds (e.g., ceramic electrodes based on TiN, $CoSi_2$, or WC).

Figure 5:
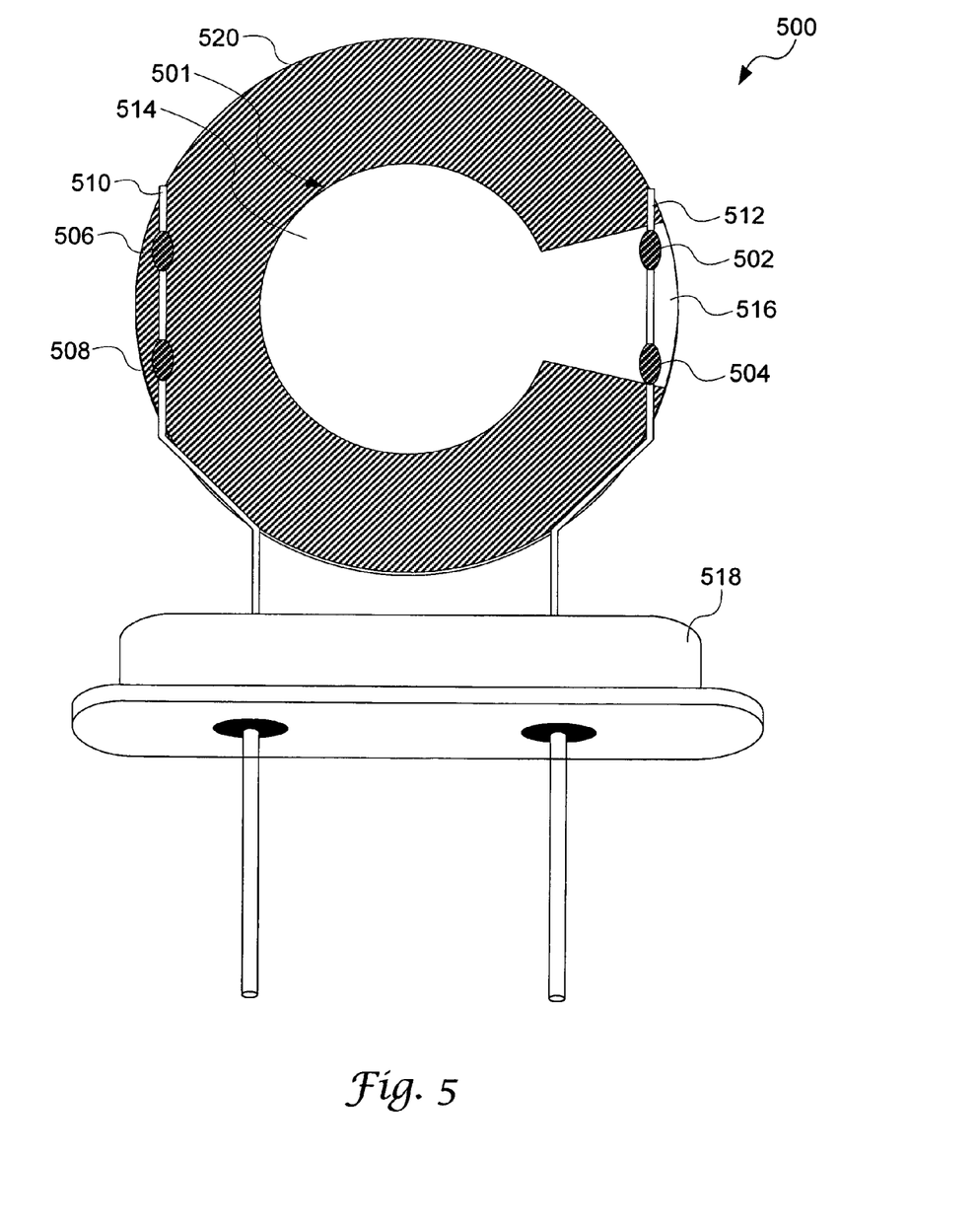
FIG. 5 illustrates a pictorial diagram of a BAW cooking oil quality sensor that can be utilized in accordance with one embodiment.

FIG. 5 illustrates a pictorial diagram of a BAW cooking oil quality sensor 500 that can be utilized in accordance with one embodiment. Sensor 500 includes a BAW sensing element 501 composed of BAW portions 514 and 516. BAW portion 516 is connected to an electrically conducting contact 512 by connectors 502, 504, which may be, for example, a solder. BAW sensing element 501 is formed on a substrate 520, which is connected to an electrically conducting contact 510 by connectors 506, 508, which may be, for example, solder. A platform 518 can be utilized to maintain contacts 510, 512 in place. Note that BAS cooking oil quality sensor 500 can also be equipped with antenna (not shown in FIG. 5) for the wireless transmission and receipt of data.

Figure 6:
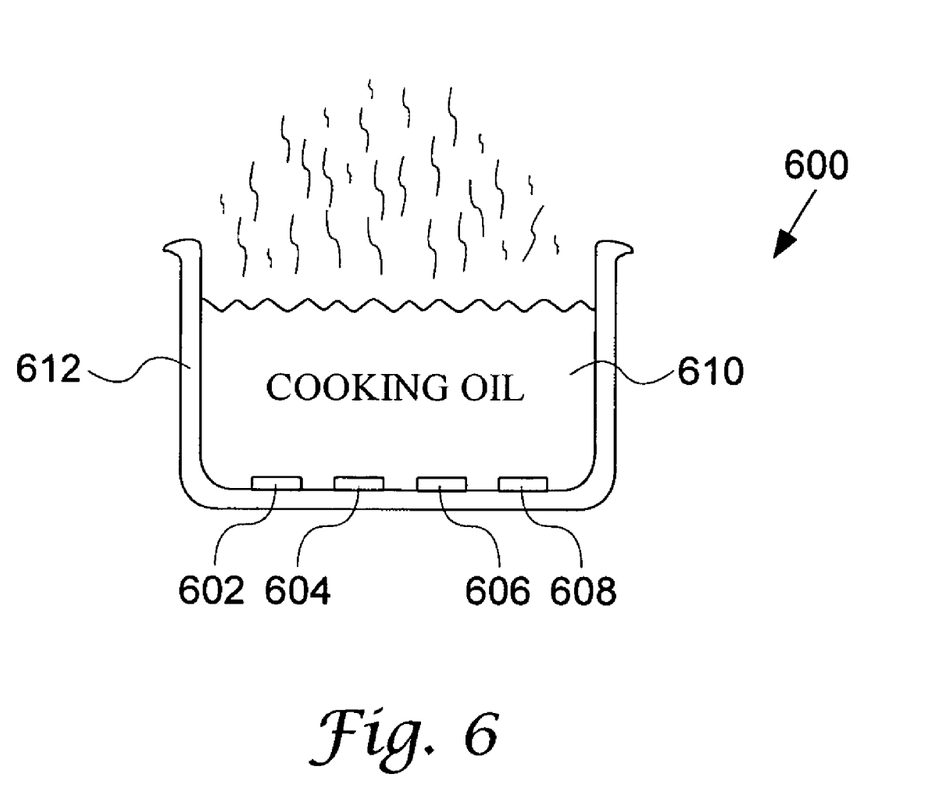
FIG. 6 illustrates a side view of a system in which one or more acoustic wave cooking oil quality sensors are incorporated into or located in a frying pan in which cooking oil is located, in accordance with a preferred embodiment.

FIG. 6 illustrates a side view of a cooking oil quality system 600 in which one or more acoustic wave cooking oil quality sensors 602, 604, 606, and 608 is incorporated into or located in a frying pan 612 in which cooking oil 610 is located, in accordance with a preferred embodiment. Note that acoustic wave sensors 602, 604, 606, and 608 can be implemented, for example, as the acoustic wave sensor 300 depicted in FIGS. 3-4 and/or the BAW sensor 500 depicted in FIG. 5, depending upon design considerations. Acoustic wave sensors 602, 604, 606, and 608 are therefore not limited to merely one type of acoustic wave sensor but can be arranged to include a variety of acoustic wave sensor types.

Sensors 602, 604, 606, and 608 can communicate wirelessly with a transmitter/receiver unit (not depicted in FIG. 6). Acoustic wave sensors 602, 604, 606, and 608 are each surrounded by a material such as that of coating 302 depicted in FIGS. 3-4. Coating 302, which is analogous to coating 102 described earlier can comprise a material that is selectively sensitive and/or reactive to fatty acids and can be used as an etch rate monitor or fatty acids monitor, depending upon design considerations. Each of the acoustic wave sensors 602, 604, 606, and 608 incorporates an antenna, such as, for example, antenna 308 depicted in FIG. 3 for the wireless transmission and receipt of data.

Depending on the type of acoustic wave sensors 602, 604, 606, and 608 utilized, such sensors can be utilized to identify acoustic waves with the cooking oil 610, including for example, bulk waves, acoustic plate mode waves, surface transverse waves, shear-horizontal acoustic plate mode waves, flexural plate waves and/or shear-horizontal surface acoustic waves. The transducers utilized with sensors 602, 604, 606, and 608 can be, for example, a bulk acoustic wave (BAW) sensing element, a shear horizontal surface acoustic wave (SH-SAW) sensing element, an acoustic plate mode (APM) sensing element, a shear horizontal acoustic plate mode (SH-APM) sensing element, a surface transverse wave (STW) sensing element and/or a flexural plate wave (FPW) sensing element, depending upon design choices.

Figure 7:
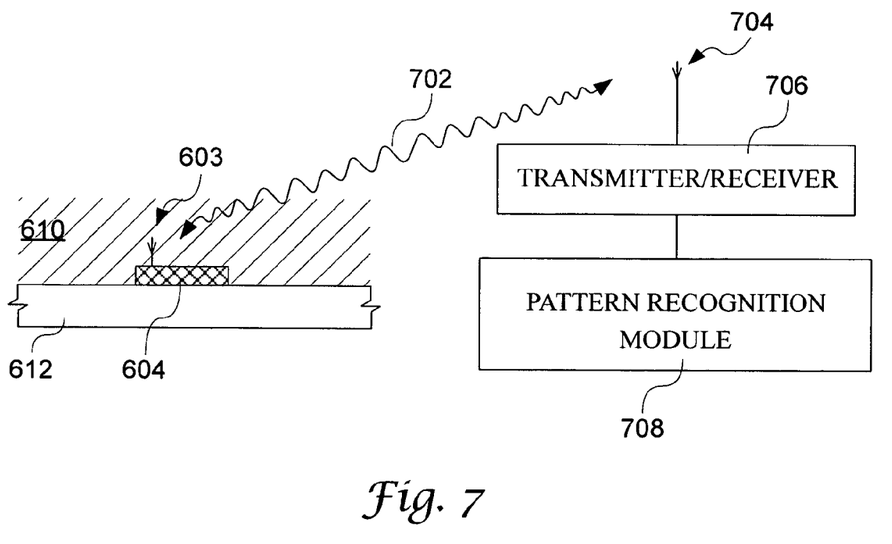
FIG. 7 illustrates a cooking oil quality detection system that includes one or more acoustic wave cooking oil sensors, in accordance with a preferred embodiment.

FIG. 7 illustrates a cooking oil quality detection system 700 that includes one or more acoustic wave cooking oil sensors such as, for example, sensor 604, in accordance with a preferred embodiment. Note that in FIGS. 6-7 identical or similar parts or elements are generally indicated by identical reference numerals. It can be appreciated, however, that both systems 600-700 can be modified to incorporate other acoustic wave sensing devices (e.g., SAW, BAW, etc.) in place of or in addition to acoustic wave sensor 604. The view depicted in FIG. 7 is therefore essentially a "close up" view of a portion of the frying pan 612 depicted in FIG. 6 with respect to acoustic wave sensor 604. In generally, acoustic wave sensor 604 comes into contact with the cooking oil 610 and through acoustic wave detecting operations thereof as described earlier can generate data indicative of the quality of the cooking coil 610. Such data can be transmitted via antenna 603 as indicated by arrow 702 to a transmitter and receiver unit 706 and its associated antenna 704. Antenna 603 is generally analogous to, for example, antenna 308 depicted in FIGS. 3-4.

The transmitter and receiver unit 706 can be optionally connected to or can communicate with a pattern recognition module 708. that can be utilized to automatically recognize varying cooking oil quality and oil degradation processes. Note that the pattern recognition module 708 can be implemented in the context of a "module". In the computer programming arts, a module can be typically implemented as a collection of routines and data structures that performs particular tasks or implements a particular abstract data type.

Modules generally can be composed of two parts. First, a software module may list the constants, data types, variable, routines and the like that can be accessed by other modules or routines. Second, a software module can be configured as an implementation, which can be private (i.e., accessible perhaps only to the module), and that contains the source code that actually implements the routines or subroutines upon which the module is based. Thus, for example, the term module, as utilized herein generally refers to software modules or implementations thereof. Such modules can be utilized separately or together to form a program product that can be implemented through signal-bearing media, including transmission media and recordable media.

Figure 8:
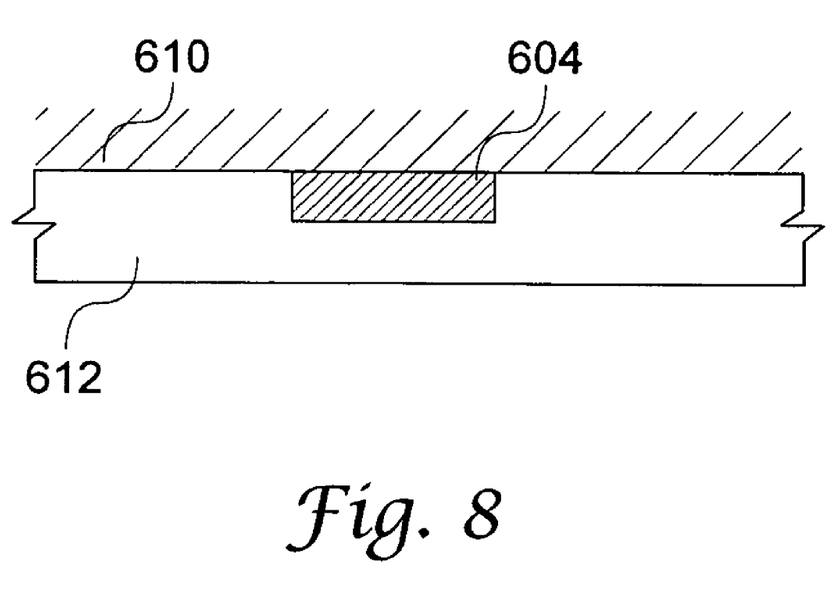
FIG. 8 illustrates a portion of the frying pan and acoustic wave sensor depicted in FIGS. 6-7, in accordance an alternative embodiment.

FIG. 8 illustrates a portion of the frying pan 612 and acoustic wave sensor 604 depicted in FIGS. 6-7, in accordance an alternative embodiment. In the configuration of FIG. 8, the acoustic wave sensor 604 is actually integrated with and/or formed into the bottom of the frying 612. FIG. 8 demonstrates that the acoustic waves sensors described herein can be provided as an attachment to the frying pan or actually integrated into the frying pan, depending of course upon design considerations.

Figure 9:
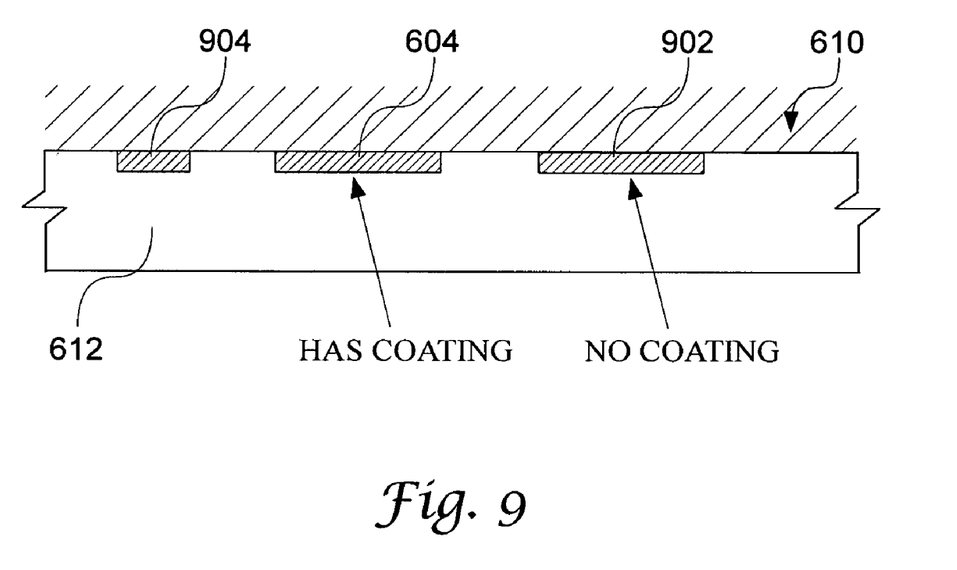
FIG. 9 illustrates a portion of the frying pan and acoustic wave sensor depicted in FIGS. 6-7, with the addition of a temperature sensor and/or a reference sensor, which can be adapted for use in accordance with an alternative embodiment.

FIG. 9 illustrates a portion of the frying pan 612 and acoustic wave sensor 604 depicted in FIGS. 6-7, with the addition of a temperature sensor 904 and/or a reference sensor 902, which can be adapted for use in accordance with an alternative embodiment. Note that in FIGS. 6-9, identical or similar parts or elements are generally indicated by identical reference numerals. Also note that reference sensor 902 is constructed in a manner similar to that of acoustic waves sensor 604 with the exception that the reference sensor does not contain the sensitive coating discussed earlier herein. The use of either temperature sensor 904 or reference sensor 902 is optional. Temperature sensor 904 generally provides temperature compensation for the generated acoustic wave data. Such data, as indicated previously, is indicative of the quality of the cooking oil. The frequency change of reference sensor 902 is generally due to temperature variations. Such frequency can be used for compensating the acoustic wave sensor, depending on design considerations.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A cooking oil quality sensing apparatus, comprising:
   an acoustic wave sensor comprising at least one acoustic wave transducer configured upon a piezoelectric substrate, wherein said acoustic wave sensor, when in contact with cooking oil, generates acoustic wave data indicative of a quality of said cooking oil;
   an antenna integrated with said acoustic wave sensor for receiving data from an external source and transmitting said acoustic wave data indicative of said quality of said cooking oil; and
   a pattern recognition module that based on at least one signal transmitted by said antenna from said acoustic wave sensor recognizes varying degrees of quality of said cooking oil.

2. The apparatus of claim 1 further comprising: a temperature sensor for providing temperature compensation for said acoustic wave data indicative of said quality of said cooking oil, wherein said temperature sensor communicates with said acoustic wave sensor.

3. The apparatus of claim 1 further comprising: a reference sensor associated with said acoustic wave sensor, wherein a frequency change of the said reference sensor due to a temperature variation is utilized for compensating said acoustic wave sensor.

4. The apparatus of claim 1 wherein said acoustic wave sensor is coated with a material that is selectively sensitive to at least one fatty acid associated with said cooking oil.

5. The apparatus of claim 1 wherein said acoustic wave sensor is coated with a material that is reactive to at least one fatty acid associated with said cooking oil.

6. The apparatus of claim 1 further comprising a frying pan for maintaining and heating said cooking oil, wherein said acoustic wave sensor is incorporated into said frying pan in order to detect acoustic wave data indicative of said quality of said cooking oil.

7. The apparatus of claim 1 further comprises a transmitter and receiver unit for transmitting data wirelessly to and from said acoustic wave sensor.

8. The apparatus of claim 1 further comprising:
   a temperature sensor for providing temperature compensation for said acoustic wave data indicative of said quality of said cooking oil, wherein said temperature sensor communicates with said acoustic wave sensor; and
   a reference sensor associated with said acoustic wave sensor, wherein a frequency change of the said reference sensor due to a temperature variation is utilized for compensating said acoustic wave sensor.

9. The apparatus of claim 1 wherein said at least one acoustic wave transducer comprises a bulk acoustic wave (BAW) sensing element, wherein a frequency associated with said BAW sensing element comprises said data indicative of said quality of said cooking oil.

10. A cooking oil quality sensing system, comprising:
    an acoustic wave sensor comprising at least one acoustic wave transducer configured upon a piezoelectric substrate, wherein said acoustic wave sensor, when in contact with cooking oil, generates acoustic wave data indicative of a quality of said cooking oil, wherein said acoustic wave sensor is coated with a material that is selectively sensitive or reactive to at least one fatty acid associated with said cooking oil;
    an antenna integrated with said acoustic wave sensor for receiving data from an external source and transmitting said acoustic wave data indicative of said quality of said cooking oil;
    a frying pan for maintaining and heating said cooking oil, wherein said antenna is incorporated into said frying pan in order to detect said acoustic wave data indicative of said quality of said cooking oil; and
    a transmitter and receiver unit for transmitting data wirelessly to and from said acoustic wave sensor, including said acoustic wave data indicative of said quality of said cooking oil;
    a temperature sensor associated with said acoustic wave sensor, wherein said temperature sensor provides temperature compensation for said acoustic wave data indicative of said quality of said cooking oil; and
    a pattern recognition module that based on at least one signal transmitted by said antenna from said acoustic wave sensor recognizes varying degrees of quality of said cooking oil.

11. The system of claim 10 further comprising a reference sensor associated with said acoustic wave sensor, wherein a frequency change of said reference sensor due to a temperature variation is utilized for compensating said acoustic wave sensor.

12. The system of claim 10 further comprising
    a reference sensor associated with said acoustic wave sensor, wherein a frequency change of said reference sensor due to a temperature variation is utilized for compensating said acoustic wave sensor, wherein said at least one acoustic wave transducer comprises a bulk acoustic wave (BAW) sensing element, wherein a frequency associated with said BAW sensing element comprises said data indicative of said quality of said cooking oil.

13. The apparatus of claim 10 wherein said at least one acoustic wave transducer comprises a bulk acoustic wave (BAW) sensing element, wherein a frequency associated with said BAW sensing element comprises said data indicative of said quality of said cooking oil.

14. A cooking oil quality sensing system, comprising:
an acoustic wave sensor comprising at least one acoustic wave transducer configured upon a piezoelectric substrate, wherein said acoustic wave sensor, when in contact with cooking oil, generates acoustic wave data indicative of a quality of said cooking oil, wherein said acoustic wave sensor is coated with a material that is selectively sensitive or reactive to at least one fatty acid associated with said cooking oil;
an antenna integrated with said acoustic wave sensor for receiving data from an external source and transmitting said acoustic wave data indicative of said quality of said cooking oil;
a frying pan for maintaining and heating said cooking oil, wherein said antenna is incorporated into said frying pan in order to detect said acoustic wave data indicative of said quality of said cooking oil;
a transmitter and receiver unit for transmitting data wirelessly to and from said acoustic wave sensor, including said acoustic wave data indicative of said quality of said cooking oil;
a temperature sensor associated with said acoustic wave sensor, wherein said temperature sensor provides temperature compensation for said acoustic wave data indicative of said quality of said cooking oil;
a reference sensor associated with said acoustic wave sensor, wherein a frequency change of said reference sensor due to a temperature variation is utilized for compensating said acoustic wave sensor;
a pattern recognition module that based on at least one signal transmitted by said antenna from said acoustic wave sensor recognizes varying degrees of quality of said cooking oil.

15. The apparatus of claim 14 wherein said at least one acoustic wave transducer comprises a bulk acoustic wave (BAW) sensing element, wherein a frequency associated with said BAW sensing element comprises said data indicative of said quality of said cooking oil.

* * * * *